United States Patent [19]

Suthanthiran

[11] Patent Number: 4,891,165

[45] Date of Patent: Jan. 2, 1990

[54] DEVICE AND METHOD FOR ENCAPSULATING RADIOACTIVE MATERIALS

[75] Inventor: Krishnan Suthanthiran, Lorton, Va.

[73] Assignee: Best Industries, Inc., Springfield, Va.

[21] Appl. No.: 225,384

[22] Filed: Jul. 28, 1988

[51] Int. Cl.$^4$ .................. G21F 9/12; G21F 9/24; A61B 17/06; B65D 85/84

[52] U.S. Cl. .................. 252/633; 250/506.1; 250/507.1; 252/644; 252/645; 128/654; 128/656; 128/659; 206/438; 206/524.1; 424/1.1; 600/1; 600/3; 600/7; 600/8

[58] Field of Search ............. 424/1.1; 252/628, 644, 252/645, 478, 633; 250/506.1, 507.1; 427/5, 6; 600/1, 3, 7, 8; 128/654, 656, 659; 206/438, 524.1, 413, 514; 376/451

[56] References Cited

U.S. PATENT DOCUMENTS

| | | | |
|---|---|---|---|
| 2,269,458 | 1/1942 | Kahn | 250/506.1 |
| 2,830,190 | 4/1958 | Karp | 250/506.1 |
| 3,145,181 | 8/1964 | Courtois et al. | 252/644 |
| 3,154,501 | 10/1964 | Hertz | 252/644 |
| 3,334,050 | 8/1967 | Grotenhuis | 252/628 |
| 3,351,049 | 11/1967 | Lawrence | 128/1.2 |
| 3,600,586 | 8/1971 | Barthelemy et al. | 424/1.1 |
| 3,632,520 | 1/1972 | Garber | 252/644 |
| 3,659,107 | 4/1972 | Selle et al. | 252/644 |
| 3,666,846 | 5/1972 | Sump et al. | 252/645 |
| 4,228,146 | 10/1980 | Imamura | 424/1.1 |
| 4,323,055 | 4/1982 | Kubiatowicz | 128/1.2 |
| 4,562,001 | 12/1985 | Vietzke et al. | 252/633 |
| 4,654,171 | 3/1987 | Boncoeur et al. | 252/633 |
| 4,726,916 | 2/1988 | Aubert et al. | 252/633 |

OTHER PUBLICATIONS

Hilaris, et al. 1988 "An Atlas of Brachytherapy", MacMillan Publishing Company, New York, pp. 55–57.

Ling et al. 1983, Physical Dosimetry of $^{125}$I Seeds of a New Design For Interstitial Implant, Int. J. Radiation Oncology Biol. Phy. vol. 9, pp. 1747–1752.

*Primary Examiner*—Howard J. Locker
*Attorney, Agent, or Firm*—Arnold, White & Durkee

[57] ABSTRACT

A capsule for encapsulating radioactive material for radiation treatment comprising two or more interfitting sleeves, wherein each sleeve comprises a closed bottom portion having a circumferential wall extending therefrom, and an open end located opposite the bottom portion. The sleeves are constructed to fit over one another to thereby establish an effectively sealed capsule structure.

22 Claims, 3 Drawing Sheets

DEVICE AND METHOD FOR ENCAPSULATING RADIOACTIVE MATERIALS

BACKGROUND

The present invention relates to capsules for and a method for encapsulating radioactive materials used for medical treatments.

Various methods for utilizing radioactive materials in radiation therapy are known. Of these, a well known method for administering the radioactive source is by the use of small radioactive "seeds". Such seeds comprise a radioactive source contained within a sealed capsule. The seeds are injected or implanted into the patient's body tissue at the site being treated.

Because these seeds are implanted in the human body, the capsule for containing these materials must be securely sealed. Otherwise, undesired leakage from the capsule may occur. The U.S. Food and Drug Administration and the U.S. Nuclear Regulatory Commission have strict requirements for encapsulation of the radioactive material to prevent leakage and resultant injury to patients and medical personnel handling such materials.

In the past the most advantageous materials for encapsulating radioactive materials included stainless steel, titanium and other low atomic number metals. However, there still exist problems of adequately sealing capsules made from these materials. Such metallic capsules are typically sealed by welding. However, welding of such small capsules is difficult. Welding such small capsules may locally increase the capsule wall thickness, or introduce higher atomic number materials at the end or ends of the capsule where the welds are located, and the presence of such localized anomalies may significantly alter the geometrical configuration at the welded end or ends, resulting in undesired shadow effects in the radiation pattern emanating from the source. Other methods of forming the capsules include drilling a capsule form in a metallic block and plugging to form a seal. However, this method suffers from the disadvantage that a capsule having uniform wall thickness is difficult to obtain, and the resulting source will not be able to uniformly distribute radiation.

Lawrence U.S. Pat. No. 3,351,049 discloses a metallic container for containing a radioactive isotope wherein the metallic container is closed and sealed by intermetallically joining the walls under pressure or by ultrasonic welding. Other techniques for welding the structure, depending on the material utilized, are also disclosed. Kubiatowicz U.S. Pat. No. 4,323,055 discloses similar methods for encapsulating radioactive material. Methods for sealing the titanium container of Kubiatowicz include laser, electron beam or tungsten inert gas welding. Kahn U.S. Pat. No. 2,269,458 discloses a somewhat primitive form of encapsulation of radioactive substances wherein the capsule is formed by screwing two threaded parts together.

All of the foregoing methods of encapsulating radioactive materials have substantial shortcomings in providing a capsule which is easy to construct while providing adequate protection against leakage, while permitting uniform radiation therethrough.

SUMMARY OF THE INVENTION

Accordingly, it is an object of the present invention to provide a new and useful method and capsule for encapsulating radioactive materials, which overcome the shortcomings of the prior art.

It is an object of the present invention to provide such a capsule for encapsulating radioactive materials which permits uniform radiation therethrough.

It is another object of this invention to provide a capsule for radiaoactive material which can be easily constructed while providing protection against undesirable leakage.

It is yet a further object of the present invention to provide a method and capsule for encapsulating radioactive materials which do not require welding in order to be adequately sealed.

The foregoing objects and others are achieved by providing a capsule for encapsulating radioactive material comprising two or more interfitting sleeves, each of said sleeves comprising a closed bottom portion having a circumferential wall portion extending therefrom and an open end opposite said bottom portion. The sleeves are constructed to fit snugly over one another to thereby provide an effectively sealed structure.

BRIEF DESCRIPTION OF THE DRAWINGS

For a better understanding of the structure, advantages and further features of the capsules for encapsulating radioactive materials of the present invention, reference is made to the accompanying drawings of various embodiments thereof, wherein.

DETAILED DESCRIPTION OF THE INVENTION

Figure 1:
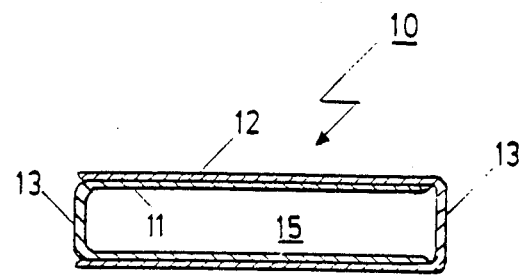
FIG. 1 is a partially schematic cross-sectional view of one preferred embodiment of the inventive capsule for encapsulating radioactive materials showing the relationship between the interfitting sleeves.
Figure 1A:
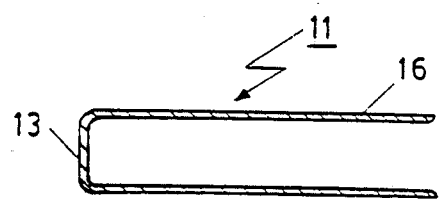
FIGS. 1A and 1B are partially schematic cross-sectional views of the individual sleeves.
Figure 1B:
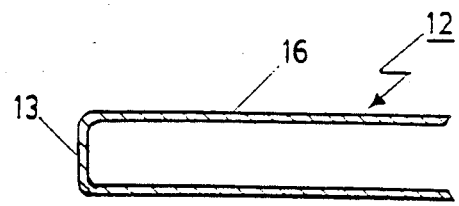

One preferred embodiment of the advantageous capsule for radioactive material of the present invention is illustrated in FIG. 1 which shows a closed capsule 10 formed from two interfitting sleeves 11 and 12. Each sleeve comprises a bottom portion 13 having a circumferential or cylindrical wall 16 extending therefrom, as illustrated in FIGS. 1A and 1B. When the sleeves are fitted together, one within the other, a substantially sealed capsule is obtained having an effectively sealed inner cavity for retaining radioactive material. The preferred shape of the sleeves is cylindrical.

The sleeves and resulting capsule are constructed of a material which provides adequate strength for thin walls and which will readily allow radiation to pass uniformly through the material. The thin walls allow for an increased amount of material to be contained in the capsule. Also desired is a material which will not easily corrode when brought into contact with body fluids. Titanium and stainless steel are among the preferred materials for forming such capsules Other suitable materials include platinum, gold, tantalum, nickel alloy, and copper or aluminum alloys having less corrosive protective coatings. Other suitable materials may have those advantageous properties and the present invention should not be construed to be limited to those materials specifically mentioned above.

The inner sleeve 11 shown in FIG. 1 is constructed to have an outer wall diameter or width which is substantially the same as the inner wall diameter of the outer sleeve 12 shown in FIG. 1B. The outer diameter of the inner sleeve 11 can range from about 0.2 mm to about 20.0 mm. The inner diameter of the outer sleeve 12 is thus chosen to be substantially the same as the outer diameter of the inner sleeve 11. Therefore, for an inner sleeve having an outer diameter of 1.0 mm, for example, the inner diameter of the outer sleeve would be 1.0 mm. When the outer sleeve 12 is fitted over the inner sleeve 11, a sealed cavity 15 is formed. The cavity 15 is capable of holding effectively radioactive material without significant leakage, due to the tight seal formed between the two sleeves 11 and 12 when they are interfitted. The sleeves may be welded or an adhesive can be applied between the sleeves, if desired.

In the embodiment shown in FIG. 1, it is desirable to construct a capsule having uniform dimensions so that radiation can pass therethrough in a relatively uniform pattern. The total thickness of sidewall 16 is substantially the same as the thickness of each bottom portion 13. When the two sleeves 11 and 12 are fitted together, a capsule is thus provided having walls of uniform total thickness. The thickness of the bottom portion 13 can vary with that of the wall portions 16, and further, the bottom portions of each sleeve can be varied so that any desired relationship between the total thickness of the walls and the bottom portions of the resulting capsule may be provided. The thickness of the bottom portions can range from about 0.05 mm to about 3.0 mm, while the thickness of the wall portions can range from about 0.03 mm to about 2.0 mm.

The walls 16 of the sleeves are constructed so that the walls of the outer sleeve 12 are slightly longer than the walls of the inner sleeve 11 by approximately the thickness of the bottom portion 13 of the inner sleeve 11. For example, when the bottom portions of the sleeves have a thickness of 0.05 mm, the walls of the outer sleeve 12 will have a length which is 0.05 mm longer than the walls of the inner sleeve 11. This construction provides an ultimate capsule having uniform thickness when the sleeves 11 and 12 are interfitted.

It will be appreciated that end portions 13 of the wall portions of each separate sleeve may be tapered toward the inner diameter of the sleeve so that insertion of the inner sleeve 11 into the outer sleeve 12 can be facilitated.

The final outer dimensions of the capsules of the present invention have outer diameters which range from about 0.25 mm to about 25.0 mm and lengths which range from about 1.1 mm to about 25.0 mm. The sealed capsule includes a source of radiation, and may also contain a radiopaque marker material for viewing the location and orientation of the sealed capsule or seed in situ in a treatment site in a patient's body. Thus, capsules can be constructed of varying sizes, including minute capsules which, because of their thin walls, can contain an effective amount of a radioactive source. The complete internal structure of such seeds is described in applicant's copending application Ser. No. 07/225,302, filed July 28, 1988, the entire disclosure of which is hereby incorporated by reference.

Figure 2:
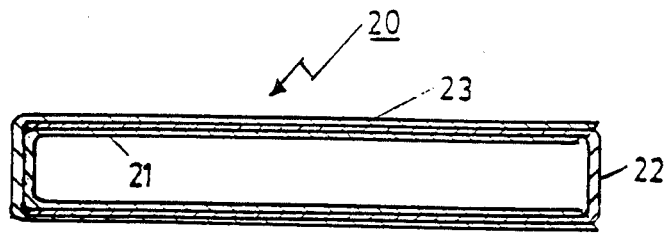
FIG. 2 is a partially schematic cross-sectional view of another preferred embodiment of the capsule of the present invention showing the relationships among the interfitting sleeves.
Figure 2A:
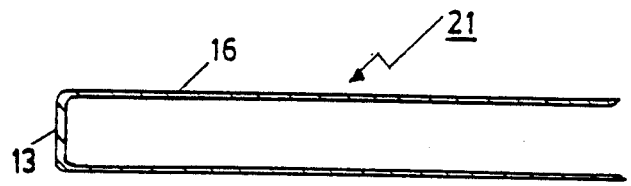
FIGS 2A, 2B, and 2C respectively are partially schematic cross-sectional views of the individual interfitting sleeves progressing outwardly.
Figure 2B:
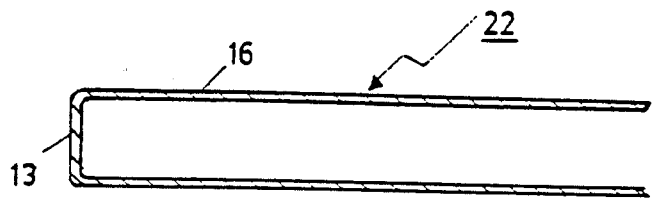
Figure 2C:
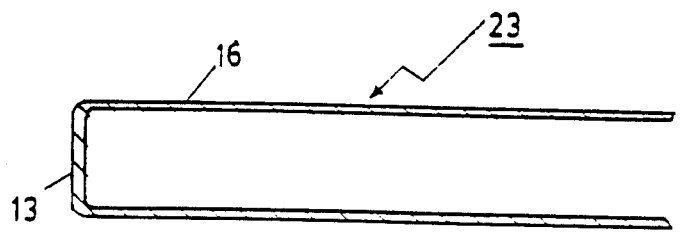

FIG. 2 shows another preferred embodiment of the capsule for radioactive materials of the present invention. In this embodiment, the capsule is constructed of three interfitting sleeves. As described with reference to the first embodiment, the sleeves are constructed so that the outer diameter of an inner sleeve is substantially the same as the inner diameter of a corresponding outer sleeve. Therefore, in the embodiment shown in FIG. 2, a capsule 20 comprising three interfitting sleeves 21, 22 and 23 is provided wherein the outer diameter of an inner sleeve is substantially the same as the inner diameter of the corresponding outer sleeve. The sleeves are interfitted so that the open end of each inner sleeve is covered by the bottom portion of the next corresponding outer sleeve.

As discussed in the description of the first preferred embodiment, the dimensions of each sleeve are chosen so that a sealed interfitting relationship between the sleeves is obtained. An outer diameter of the innermost sleeve 21 can range from about 0.2 mm to about 20.0 mm. An inner diameter of the next interfitting sleeve 22 is chosen to be substantially the same as the outer diameter of the innermost sleeve 21. Likewise, the inner diameter of the outermost sleeve 23 is chosen so as to be substantially the same as the outer diameter of the sleeve 22. It will be appreciated that the diameters of each sleeve are dependent upon the thickness of the walls of each sleeve, which thickness can vary.

The thickness of the bottom portions 13 are preferably the same as the total thickness of the sleeve walls. However, the thickness of the bottom portion 13 of the sleeve 22 may be made thicker than the bottom portions 13 of the sleeves 21 and 23. Therefore, the thicknesses of the bottom portions and walls can be made such that a uniform overall thickness of encapsulation is provided around the inner cavity of the capsule when all the sleeves are interfitted.

The lengths of the walls of each succeeding sleeve increase to compensate for the thickness of the bottom portion of each sleeve. The lengths of the walls of the innermost sleeve 21 will be the least for the sleeves 21, 22 and 23. The length of the walls of the innermost sleeve 21 can be as short as about 1.0 mm. The length of the walls of the sleeve 22 will be increased to compensate for the thickness of the bottom portion 13 of sleeve 21. Likewise, the length of the walls of the outermost sleeve 23 will increase depending on the total thicknesses of the bottom portions 13 of sleeves 21 and 22.

As in the first preferred embodiment, a capsule according to the second embodiment can be constructed having final outer dimensions of about 1.1 mm to about 25.0 mm in length and about 0.25 mm to about 25.0 mm in diameter.

It should be appreciated that the materials of each sleeve do not have to be the same. Sleeves of different materials can be interfitted to provide a tightly sealed capsule.

Figure 3:
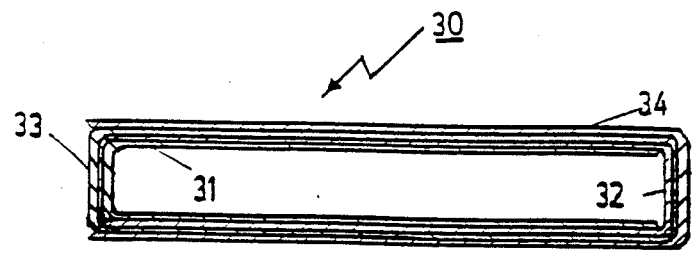
FIG. 3 is a partially schematic cross-sectional view of still another preferred embodiment of the capsule for radioactive materials of the present invention.
Figure 3A:
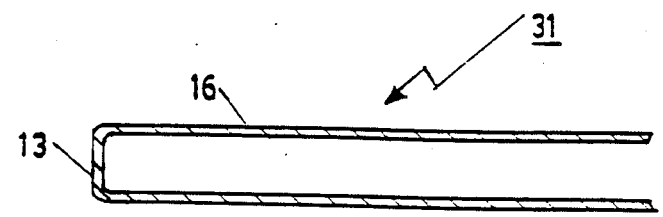
FIGS. 3A, 3B, 3C, and 3D respectively are partially schematic cross-sectional views of the individual interfitting sleeves progressing outwardly.
Figure 3B:
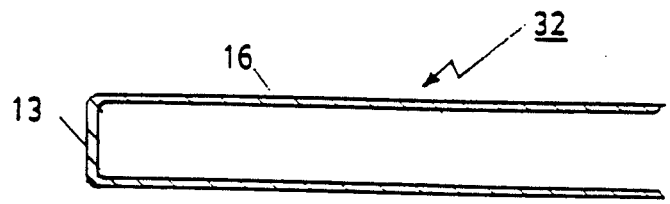
Figure 3C:
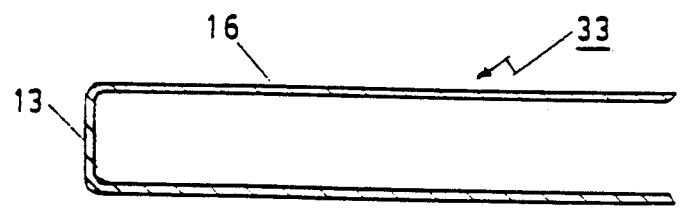
Figure 3D:
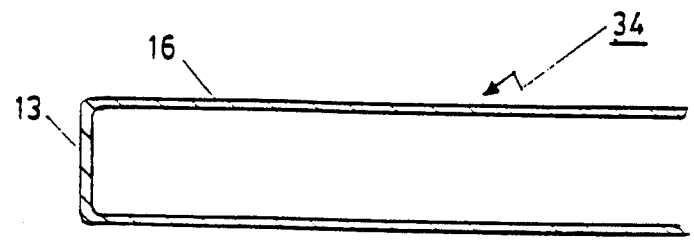

Another embodiment of the capsule of the present invention is illustrated in FIG. 3. In this embodiment, a capsule 30 is provided having four interfitting sleeves 31, 32, 33 and 34. The innermost sleeve 31 of this embodiment comprises a bottom portion 13 having a wall portion extending therefrom. An open end is provided opposite to that of the bottom portion. The next sleeve 32 has the same construction as the innermost sleeve 31 except that the innermost diameter of the sleeve 32 is substantially the same as the outer diameter of the sleeve 31. Furthermore, the length of the wall of the sleeve 32 is longer than the length of the wall of the inner sleeve 31 by about the thickness of the bottom portion 13. Likewise, the sleeve 33 of the capsule of this embodiment has an inner diameter which is substantially the same as the outer diameter of the sleeve 32. Furthermore, the length of the wall of the sleeve 33 is longer than the length of the wall of the sleeve 32 by approximately the thickness of the bottom portion 13 of the sleeve 32. The outermost sleeve 34 has an inner diameter which is substantially the same as the outer diameter of the sleeve 33. The length of the wall of the outermost sleeve 34 is longer than the wall of the sleeve 33 by about the thickness of the bottom portion 13 of the sleeve 33. The capsule is constructed by fitting each of the corresponding sleeves in a manner wherein the open end of one sleeve is oriented at the closed end of a corresponding sleeve. When interfitted, the sleeves provide a capsule having an inner cavity which is surrounded uniformly by the walls created by this interfitting relationship.

Each sleeve in this embodiment may comprise a material different than that of another sleeve. It may be desired to construct a capsule wherein the sleeves 31 and 32 are of one material to contain the radioactive substance while the sleeves 33 and 34 are of a material which is highly resistant to corrosion or deterioration by body fluids. Other combinations of materials can be envisioned depending upon the particular use of the capsule and the material to be contained therein.

While the foregoing descriptions of the advantageous capsule for radioactive material have described various embodiments thereof with various materials, thicknesses, sizes and orientations, it will be appreciated by those skilled in the art that various modifications ca be made in such capsules without departing from the scope or spirit of the invention as stated in the following claims.

What is claimed is:

1. A small, metallic capsule for encapsulating radioactive materials for medical and industrial diagnostic, therapeutic and functional applications, comprising:
   at least first and second metallic sleeves, each of said sleeves comprising a bottom portion having a circumferential wall extending therefrom, and having an open and opposite said bottom portion;
   wherein said first sleeve has an outer surface which is complementary to and substantially the same size as the inner surface of said second sleeve, said second sleeve fitting snugly over the open end of said first sleeve, thereby forming a substantially sealed, closed capsule, having an inner cavity, with substantially uniform total wall thickness permitting substantially uniform radiation therethrough.

2. The capsule of claim 1, wherein said sleeves are cylindrical.

3. The capsule of claim 1 wherein said sleeves comprise a material selected from the group consisting of titanium, stainless steel, platinum, gold, tantalum, and copper or aluminum alloys, said copper and aluminum alloys having a protective coating.

4. The capsule of claim 1 wherein said sleeves comprise a material selected from the group consisting of titanum and stainless steel.

5. The capsule of claim 1 wherein the wall of said inner sleeve extends substantially to the bottom portion of said second sleeve.

6. The capsule of claim 1, further comprising a third sleeve comprising a bottom portion having a circumferential wall extending therefrom, and having an open end opposite to said bottom portion of said third sleeve wherein and third sleeve has an inner surface which is complementary to and substantially the same size as the outer surface of said second sleeve, said third sleeve fitting snugly over the open end of said second sleeve.

7. The capsule of claim 6, further comprising a fourth sleeve comprising a bottom portion having a circumferential wall extending therefrom, and having an open end opposite said bottom portion of said fourth sleeve, wherein said fourth sleeve has an inner surface which is complementary to and substantially the same size as the outer surface of said third sleeve, said fourth sleeve fitting snugly over the open end of said third sleeve.

8. The capsule of claim 7, wherein the length of the wall of said second sleeve is longer than the length of the wall of said first sleeve by a distance which is about the same as the thickness of the bottom portion of said first sleeve.

9. The capsule of claim 7, wherein the length of the wall of said third sleeve is longer than the length of the wall of said second sleeve by a distance which is about the same as the thickness of the bottom portion of said second sleeve.

10. The capsule of claim 7, wherein the length of the wall of said fourth sleeve is longer than the length of the wall of said third sleeve by a distance which is about the same as the thickness of the bottom portion of said third sleeve.

11. The capsule of claim 1, wherein the thickness of the bottom portion of each sleeve is in the range of about 1 to 2 times the thickness of the wall portions of each sleeve.

12. The capsule of claim 1, wherein the lengths of said sleeves ranges from about 1.0 mm to about 25.0 mm.

13. The capsule of claim 6, wherein the lengths of said sleeves range from about 1.0 mm to about 25.0 mm.

14. The capsule of claim 7, wherein the lengths of said sleeves range from about 1.0 mm to about 25.0 mm.

15. The capsule of claim 1, wherein the thickness of circumferential walls of said sleeves ranges from about 0.2 mm to about 2.0 mm.

16. The capsule of claim 1, wherein the thickness of the bottom portions of said sleeves ranges from about 0.2 mm to about 3.0 mm.

17. The capsule of claim 1, wherein the width of said sleeves range from about 0.25 mm to about 25.0 mm.

18. The capsule of claim 6, wherein the width of said sleeves range from about 0.25 mm to about 25.0 mm.

19. The capsule of claim 7, wherein the width of said sleeves range from about 0.25 mm to about 25.0 mm.

20. The capsule of claim 1, wherein the sleeves are further connected by welding or adhesive.

21. The capsule of claim 6, wherein the sleeves are further connected by welding or adhesive.

22. The capsule of claim 7, wherein the sleeves are further connected by welding or adhesive.

* * * * *